(12) United States Patent
Harel et al.

(10) Patent No.: US 7,378,531 B2
(45) Date of Patent: May 27, 2008

(54) PROCESS FOR THE PREPARATION OF VALSARTAN

(75) Inventors: Zvi Harel, Kfar Saba (IL); Igor Rukhman, Technion (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 286 days.

(21) Appl. No.: 10/829,870

(22) Filed: Apr. 21, 2004

(65) Prior Publication Data

US 2005/0010053 A1    Jan. 13, 2005

Related U.S. Application Data

(60) Provisional application No. 60/557,497, filed on Mar. 30, 2004, provisional application No. 60/537,994, filed on Jan. 21, 2004, provisional application No. 60/512,557, filed on Oct. 16, 2003, provisional application No. 60/471,871, filed on May 20, 2003, provisional application No. 60/464,197, filed on Apr. 21, 2003.

(51) Int. Cl.
    *C07D 257/00* (2006.01)
(52) U.S. Cl. ..................................... 548/253
(58) Field of Classification Search ................. 548/253
    See application file for complete search history.

(56) References Cited

U.S. PATENT DOCUMENTS

| | | | |
|---|---|---|---|
| 5,260,325 A | 11/1993 | Markwalder et al. | |
| 5,399,578 A | 3/1995 | Buhlmayer et al. | |
| 5,965,592 A | 10/1999 | Buhlmayer et al. | |
| 6,271,375 B1 | 8/2001 | Villa et al. | |
| 6,294,197 B1 | 9/2001 | Wagner et al. | |
| 6,395,728 B2 | 5/2002 | Webb et al. | |
| 6,465,502 B1 | 10/2002 | Bullock et al. | |
| 6,485,745 B1 | 11/2002 | Wagner et al. | |

| | | |
|---|---|---|
| 2002/0132839 A1 | 9/2002 | Ganter et al. |
| 2003/0035832 A1 | 2/2003 | Katakuse et al. |
| 2003/0152620 A1 | 8/2003 | Ganter et al. |
| 2003/0207930 A1 | 11/2003 | Marti et al. |
| 2004/0072886 A1 | 4/2004 | Reguri et al. |
| 2004/0242661 A1 | 12/2004 | Rukhman et al. |
| 2005/0059827 A1 | 3/2005 | Rukhman et al. |

FOREIGN PATENT DOCUMENTS

| | | |
|---|---|---|
| EP | 0 570 091 A1 | 11/1993 |
| EP | 0 443 983 B1 | 2/1996 |
| WO | WO 97/30036 | 8/1997 |
| WO | WO 99/01459 A | 1/1999 |
| WO | WO 99/67231 | 12/1999 |
| WO | WO 01/82858 A2 | 11/2001 |
| WO | WO 01/82858 A3 | 11/2001 |
| WO | WO 02/06253 A1 | 1/2002 |
| WO | WO 03/070246 A1 | 8/2003 |
| WO | WO 03/089417 | 10/2003 |
| WO | WO 2004/026847 | 4/2004 |
| WO | WO 2004/083192 A1 | 9/2004 |
| WO | WO 2004/087681 A1 | 10/2004 |
| WO | WO 2004/094392 A1 | 11/2004 |
| WO | WO 2005/089720 A1 | 9/2005 |
| WO | WO 2005/102987 A1 | 11/2005 |

OTHER PUBLICATIONS

Peter Buhlmayer, et al., *Bioorgan.& Med. Chem. Lett.*, 4(1), 29-34 (1994).
Th.Moenius, et al., *J.Labelled Cpd. Radiopharm.*, 43(13) 1245-1252 (2000).
Qingzhong Jia, et al., *Zhongguo Yiyao Gongye Zazhi*, 32(9) 385-387 (2001).
Borka L., et al., "Crystal Polymorphism of Pharmaceuticals", *Acta Pharm. Jugosl.*, 40, (1990) 71-94.
Merck Index (12th Edition, p. 1691, Valsartan n. 10051).
Zhong Guo, et al. Chinese Journal of Pharmaceuticals, 2002, pp. 385-387, vol. 32, part 9.

*Primary Examiner*—Rei-tsang Shiao
(74) *Attorney, Agent, or Firm*—Kenyon & Kenyon LLP

(57) ABSTRACT

Provided is a process for preparing valsartan and precursors thereof.

13 Claims, No Drawings

PROCESS FOR THE PREPARATION OF VALSARTAN

PRIORITY

This application claims the benefit of U.S. provisional application Ser. No. 60/537,994, filed Jan. 21, 2004; U.S. provisional application Ser. No. 60/557,497 filed Mar. 30, 2004; U.S. provisional application Ser. No. 60/512,557, filed Oct. 16, 2003; U.S. provisional application Ser. No. 60/471,871, filed May 20, 2003; and U.S. provisional application Ser. No. 60/464,197, filed Apr. 21, 2003, the contents of all of which are incorporated herein.

FIELD OF THE INVENTION

The present invention relates to a process for preparing valsartan and precursors thereof.

BACKGROUND

Valsartan, also known as (S)—N-(1-Carboxy-2-methyl-prop-1-yl)-N-pentanoyl-N-[2'-(1H-tetrazol-5-yl)bi phenyl-4-ylmethyl]-amine, has the following structure:

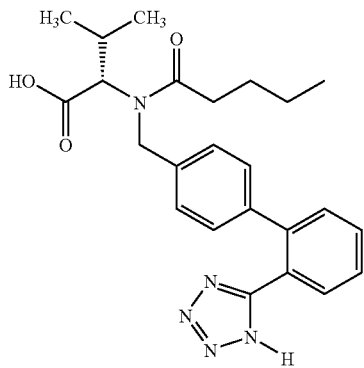

| Formula | $C_{24}H_{29}N_5O_3$ |
|---|---|
| Molecular Mass | 435.52 |
| Exact Mass | 435.227040 |
| Composition | C 66.19% H 6.71% N 16.08% O 11.02 |
| Melting Range | 105-110° C. | and is marketed as the free acid under the name DIOVAN. DIOVAN is prescribed as oral tablets in dosages of 40 mg, 80 mg, 160 mg and 320 mg of valsartan.

Valsartan and/or its intermediates are disclosed in various references, including: U.S. Pat. Nos. 5,399,578, 5,965,592, 5,260,325, 6,271,375, WO 02/006253, WO 01/082858, WO 99/67231, WO 97/30036, Peter Bühlmayer, et. al., Bioorgan. & Med.

Chem. Let., 4(1) 29-34 (1994), Th. Moenius, et. al., J. Labelled Cpd. Radiopharm., 43(13) 1245-1252 (2000), and Qingzhong Jia, et. al., Zhongguo Yiyao Gongye Zazhi, 32(9) 385-387 (2001).

Valsartan is an orally active specific angiotensin II antagonist acting on the AT1 receptor subtype. Valsartan is prescribed for the treatment of hypertension. U.S. Pat. No. 6,395,728 is directed to use of valsartan for treatment of diabetes related hypertension. U.S. Pat. Nos. 6,465,502 and 6,485,745 are directed to treatment of lung cancer with valsartan. U.S. Pat. No. 6,294,197 is directed to solid oral dosage forms of valsartan. These patents are incorporated herein by reference.

The synthesis of valsartan is discussed, inter alia, in U.S. Pat. No. 5,399,578, which is incorporated herein in its entirety by reference. In the synthesis disclosed therein, the final synthetic step (exclusive of work-up and purification) involves the reaction of a cyano group on the biphenyl ring with an azide, for example, tributyl tin azide. The reaction scheme of the '578 patent is as follows:

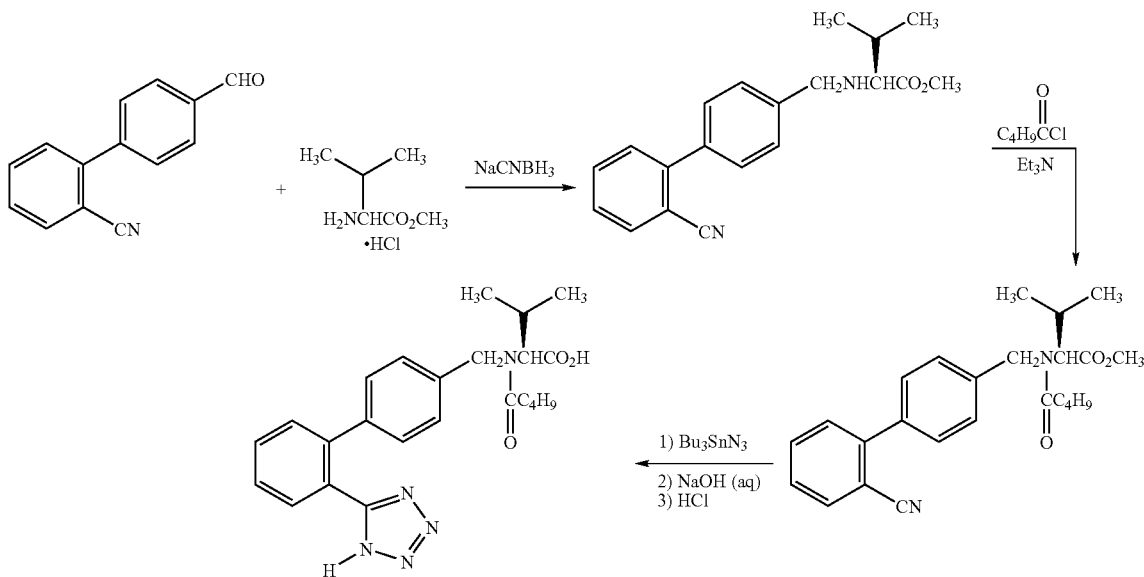

The starting compound in the '578 patent is made as follows:
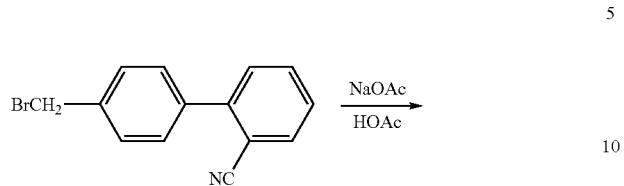
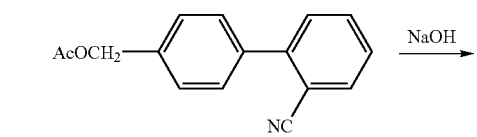
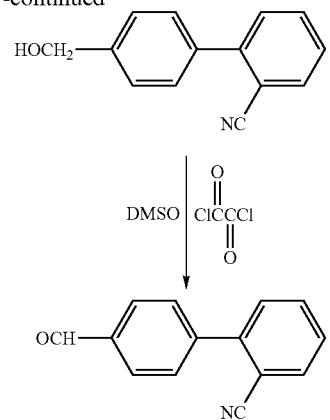
Peter Bühlmayer, et. al., Bioorgan. & Med. Chem. Let., 4(1) 29-34 (1994)
In Moenius, et. al., J. Labelled Cpd. Radiopharm., 43(13) 1245-1252 (2000), various schemes for synthesis of valsartan are provided, with one being:
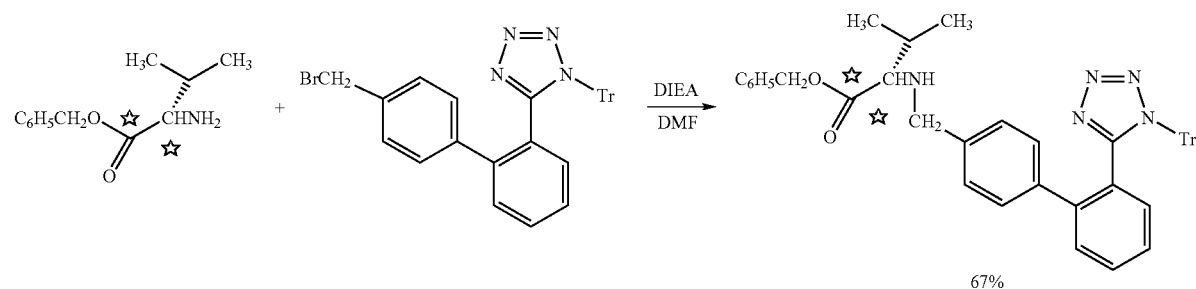
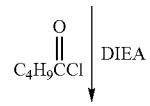
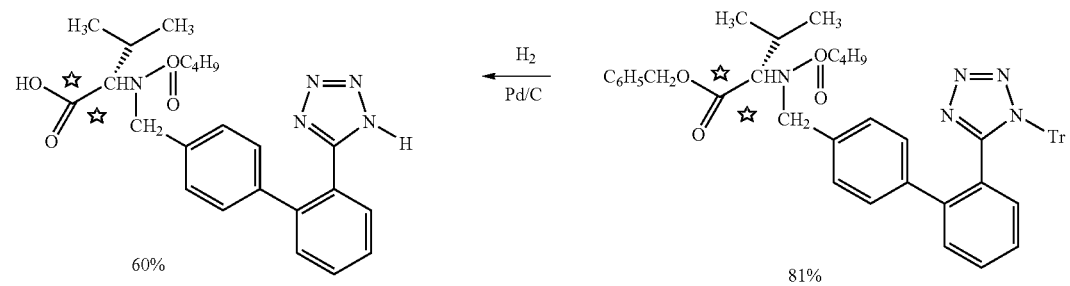

Another paper, Qingzhong Jia, et. al., Zhongguo Yiyao Gongye Zazhi, 32(9) 385-387 (2001), discloses a synthesis scheme for valsartan as follows:

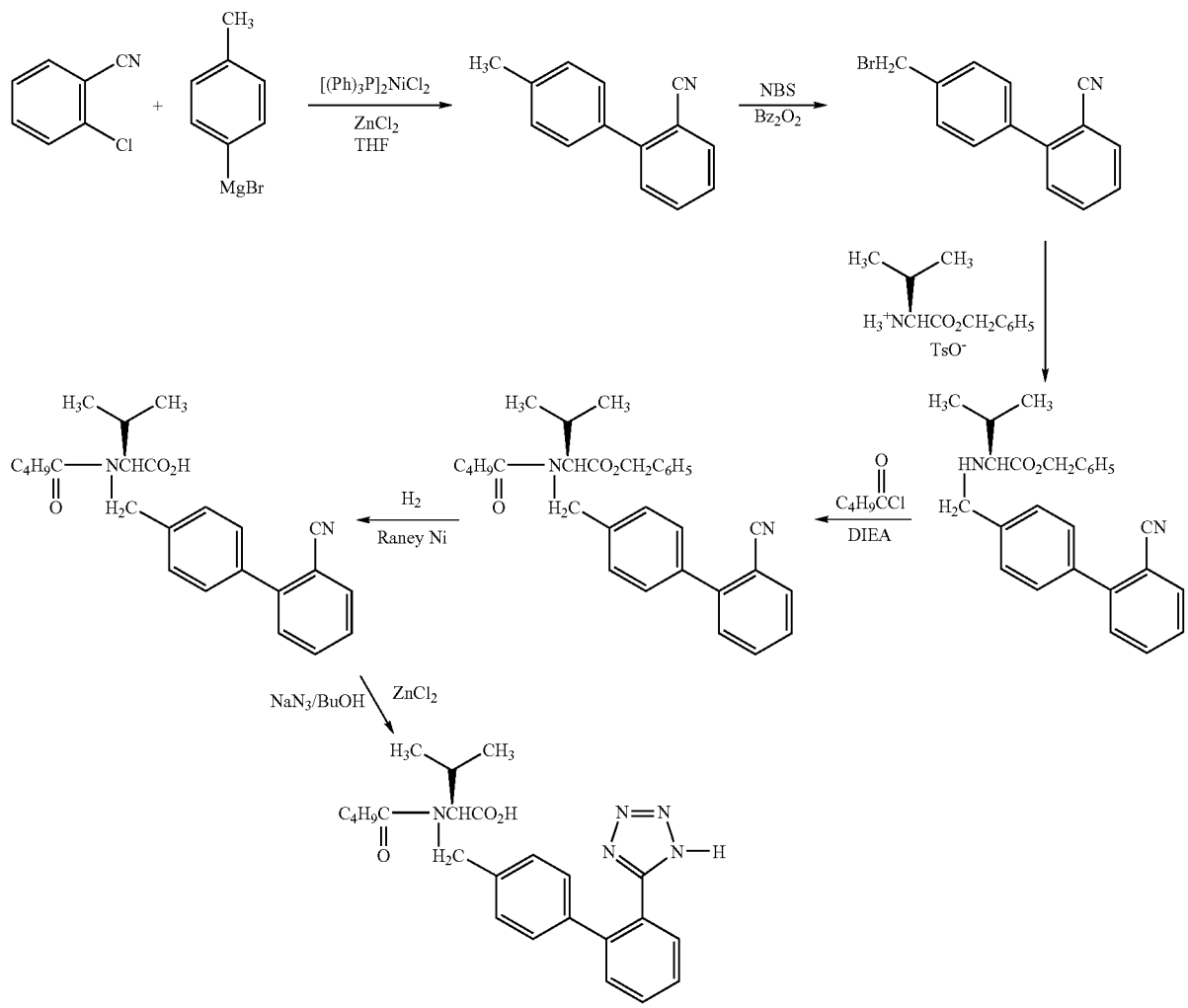

There is a need in the art for an improved synthetic process for the preparation of valsartan and precursors of valsartan.

OBJECTS AND SUMMARY OF THE INVENTION

In one embodiment, the present invention provides valsartan substantially free of its isoleucine analogue.

In another embodiment, the present invention provides a method for preparing valsartan substantially free of its isoleucine analogue. This method includes starting with a sample of valine or valine derivative, preferably L-valine methyl ester, comprising a sufficiently low level of the isoleucine derivative, preferably L-isoleucine methyl ester. Preferably, the amount of the isoleucine derivative in the valine or valine derivative sample is less than about 0.1% as rear percentage GC. This method comprises:

a) obtaining one or more samples of one or more batches of valine or its derivative;

b) measuring the level of isoleucine or corresponding isoleucine derivative in each of the samples of step (a);

c) selecting the valine or valine derivative batch that comprises a level of isoleucine or isoleucine derivative of less than about 0.1% as area percentage GC based on the measurement or measurements conducted in step (b); and d) using the batch selected in step (c) to synthesize said valsartan.

In a preferred embodiment, the valine or valine derivative sample has an amount of less than about 0.07% as area percentage GC of its isoleucine analogue.

The level of the isoleucine derivative in the valine sample can be determined using standard analytical techniques known to those of ordinary skill in the art. For example, the level of the isoleucine derivative may be determined by GC.

Valsartan is synthesized by methods such as described in U.S. Pat. No. 5,399,578, hereby incorporated by reference.

In another aspect, the present invention provides a process for preparing valsartan comprising synthesizing valsartan from a sample of valine or a valine derivative, wherein the process analyzes the level of isoleucine or its derivative present in an initial sample of valine or its derivative at least at a single stage during the synthetic process to control amount of the corresponding isoleucine impurity present in valsartan.

In another aspect, the present invention provides a process for preparing valsartan comprising the steps of:
a) analyzing a $C_1$ to $C_4$ alkyl ester of L-valine for presence of its isoleucine analogue as an impurity;
b) selecting a sample that has NMT about 0.1% as area percentage GC of the isoleucine analogue of L-valine as determined by HPLC;

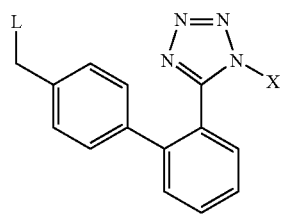

G2 c) reacting compound G2:
with the L-valine ester in a first organic solvent to obtain a compound G3:

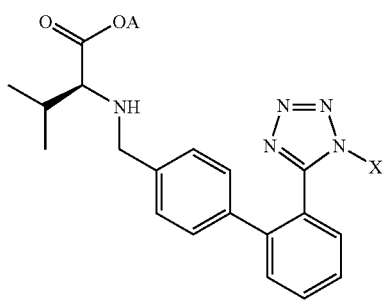

G3 d) reacting compound G3 with an acylating agent in a second organic solvent to obtain a compound G4;

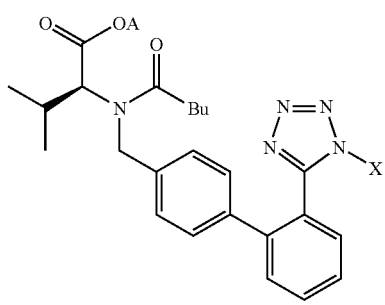

G4 and
e) hydrolyzing compound G4 to obtain valsartan.
wherein A is a $C_1$ to $C_4$ alkyl ester, X is a trityl group and L is a leaving group.

DETAILED DESCRIPTION OF THE INVENTION

The levels of isoleucine analogue of valine were analyzed by GC. The levels of isoleucine analogue in valsartan were analyzed by HPLC.

The presence of impurities in valsartan may pose a problem for formulation in that impurities often affect the safety and shelf life of a formulation. The present invention provides a method for ameliorating the effect of a single impurity present in formulations of valsartan by reducing the amount of the impurity during synthesis. The impurity, the isoleucine analogue of L-valine, has not been disclosed in the literature and has the following structure:

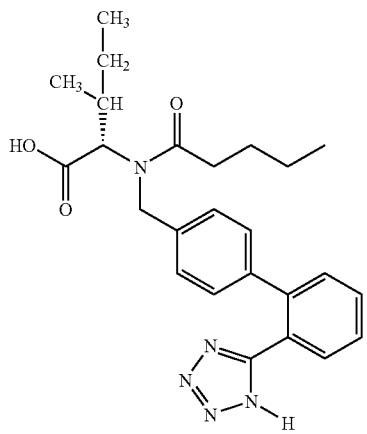

Two samples of Valsartan were prepared by the described procedure (examples 1-3) of the present invention from Valine Methyl ester of different suppliers. The sample from supplier A contained 0.131% as area percentage GC of isoleucine methyl ester and the sample from supplier B (Kony Pharma China) contained 0.07% as area percentage GC of the ester by GC as area percentage (for method see analytical part). The Valsartan prepared from valine methyl ester of supplier A contained 0.13% as area percentage HPLC of isoleucine analogue and valsartan prepared from supplier B contained 0.07% as area percentage HPLC of the isoleucine analogue (for HPLC method see analytical part). These results are in good correlation with GC data of the starting Valine Methyl Esters, suggesting that the isoleucine impurity present in the starting material would also be present in the final product in the same ratio.

Accordingly, the present invention provides a process for preparing valsartan having a low level of the isoleucine analogue as an impurity by checking for the impurity in the starting material and choosing starting material which has a low level of the impurity. See e.g. WO/03070246, incorporated herein by reference. In one embodiment, a sample of VLS-07 having a level of the impurity of NMT about 0.1% as area percentage GC, more preferably NMT about 0.07% is chosen. The relative retention time (RRT) of the isoleucine analogue of VLS-07 compared to VLS-02 is 1.2. Instead of choosing VLS-07, other batches of intermediates such as VLS-04 and VLS-05 may be tested for the amount of the impurity, and the batches discarded if the requisite amount of impurity is not met.

If the requisite amount of impurity is not met, it may be possible to purify the starting material or intermediates by techniques such as crystallization. See e.g. WO/03070246.

The method of the present invention may be applied to any synthesis method known in the art, such as that disclosed in U.S. Pat. No. 5,399,578. In a preferred embodiment illustrated in the present invention, the synthesis of valsartan is carried out by reacting a 5-(4'bromomethylbiphenyl-2-yl)-1H-tetrazole with an L-valine derivative substantially free of its isoleucine analogue. The L-valine derivative may be any suitable derivative, including but not limited to addition salts, ethers and esters of L-valine. Preferred esters include methyl, ethyl, propyl, butyl (including t-butyl), benzyl and aryl esters. A most preferred ester is a $C_1$ to $C_4$ alkyl ester, particularly methyl or t-butyl ester.

The reaction is preferably carried out in an organic solvent. Examples of preferred organic solvents include, but are not limited to, N,N dimethyl formamide (DMF), dimethyl acetamide (DMA), toluene, hexane, 1,2-dimethoxyethane (DME), diethoxymethane, tetrahydrofuran (THF), benzene, m-xylene, ethyl acetate, o-xylene, tetralins, formals, glymes and mixtures thereof. Other hydrocarbons useful in the practice of the present invention will be apparent to the skilled artisan.

The synthesis of valsartan of the present invention may include the step of reacting a 5-(4'bromomethylbiphenyl-2-yl)-1H-tetrazole with an L-valine derivative. A preferred 5-(4'bromomethylbiphenyl-2-yl)-1H-tetrazole is 5-(4'bromomethylbiphenyl-2-yl)-1-trityl-1H-tetrazole (VLS-02). A preferred L-valine derivative is L-valine methyl ester (VLS-07). The step is carried out in an organic solvent reaction system. To the organic solvent is added an amount of a basic material. The basic material may be a carbonate salt of an alkali metal or an organic base. Preferred salts of alkali metals include sodium carbonate and potassium carbonate. Preferred organic bases include triethanolamine, diethanolamine, triethylamine and diethylamine. As described above the organic solvent is preferably selected from DMF, DMA, toluene, hexane, DME, diethoxymethane, THF, benzene, m-xylene, o-xylene, ethyl acetate, tetralins, formals, glymes and mixtures thereof. A most preferred organic solvent is acetonitrile. The reaction may optionally be carried out in the presence of a catalyst. Preferred solvents for use with a phase transfer catalyst are toluene and ethyl acetate. VLS-07 is added to the solvent/base mixture. VLS-02 is added, preferentially in three separate portions, to the reaction mixture, and the resulting reaction mixture is heated with agitation for a reaction time of between 1 to 6 hours.

After the reaction time, the reaction system is cooled, and the solvent is removed to yield the crude residue of N-valine methyl ester 5-(4'methylbiphenyl-2-yl)-1-trityl-1H-tetrazole reaction product (VLS-04). Typically the solvent is removed by evaporation under reduced pressure.

In addition to bromine in VLS-02, other leaving groups may be utilized, including other halogens such as chlorine, or sulfonates. The acylating agent used may also include other leaving groups.

In a second step of the synthetic method of the present invention, the N-valine methyl ester 5-(4'methylbiphenyl-2-yl)-1-trityl-1H-tetrazole reaction product (VLS-04) is reacted with an acylating agent to form a valsartan precursor such as (S)-N-(1-carboxymethoxy-2-methyl-prop-1-yl)-N-pentanoyl-N-[2'-(1-trityl-1H-tetrazol-5-yl)bi phenyl-4-yl methyl]-amine (VLS-05). Crude residue produced in the synthetic step described above is dissolved in a suitable organic solvent. The organic solvent preferably contains an amount of an organic basic material. Preferred organic basic materials include triethylamine and tributylamine. Preferred organic solvents include toluene, DMA, DMF, hexane and acetonitrile. A most preferred organic solvent is dry toluene. To the resulting solution is added an acylating agent. Preferably the acylating agent is valeroyl chloride. The resulting mixture is agitated at room temperature for a period of from about 12 to about 24 hours. Preferably the reaction mixture is agitated for a period of about 20 hours. The time of the acylation reaction can be conveniently monitored using thin layer chromatography. Following completion of the reaction, the reaction mixture is neutralized with a molar excess of base, preferably aqueous $NaHCO_3$, and the resulting two-phase reaction system is separated. The organic phase is washed and dried, and the reaction product, (S)-N-(1-carboxymethoxy-2-methyl-prop-1-yl)-N-pentanoyl-N-[2'-(1-trityl-1H-tetrazol-5-yl)biphenyl-4-yl methyl]-amine, (VLS-05), separated out. The separation may be carried out by any known method, but is typically carried out by evaporation under reduced pressure. The reaction product may be purified by, for example, chromatographic means, prior to further use in the synthesis.

In a third step of the synthetic method of the present invention the protecting groups, e.g., the trityl group attached to the tetrazole ring and the L-valine substituent (such as the methyl ester group of L-valine methyl ester (VLS-07)), can be cleaved to produce valsartan (VLS-00), or an analogue thereof. Crude residue produced in the synthetic step described above is dissolved in a suitable water-miscible solvent. A solvent is water miscible if it is miscible with water at least in any proportion from 80:20 to 20:80 (weight basis). Preferred water-miscible solvents include acetone, methyl ethyl ketone (MEK), acetonitrile, tetrahydrofuran (THF), dioxane and $C_1$ to $C_4$ alcohols. Acetone is a most preferred water-miscible solvent. The resulting solution is acidified and agitated at a temperature of from about 0° C. to about 40° C. Most preferably the temperature is about room temperature. The time of the cleavage reaction can be conveniently monitored using thin layer chromatography. An aqueous solution of a basic material is added and the water-miscible solvent is evaporated, preferably at reduced pressure. Suitable basic materials include potassium hydroxide, potassium carbonate and sodium hydroxide. The trityl alcohol formed is separated and the liquid phase is acidified by addition of a suitable acid to a pH of about 3. Preferred acids include mineral acids, hydrogen sulfate, trifluoroacetic acid, formic acid, hydrobromic acid and acetic acid. A most preferred acid is hydrochloric acid. The resulting suspension is extracted with ethyl acetate and the crude product, for example, (S)-N-(1-carboxymethoxy-2-methyl-prop-1-yl)-N-pentanoyl-N-[2'-(1H-tetrazol-5-yl) biphenyl-4-yl methyl]-amine, (VLS-06), recovered by, for example, evaporation under reduced pressure. The resulting product is dissolved in an organic solvent. Preferred organic solvents include organic alcohols, acetone and acetonitrile. A most preferred solvent is acetone. The resulting solution is cooled to a temperature of between about −10° C. and about 45° C. Preferably the resulting solution is cooled to a temperature of between about 0° C. and about 4° C. The acid is neutralized with a molar excess of base, preferably aqueous KOH, and the water-miscible solvent is evaporated, preferably at reduced pressure. The time of the cleavage reaction can be conveniently monitored using thin layer chromatography or HPLC monitoring. The solution is extracted with ethyl acetate and acidified by addition of a suitable acid to a pH of about 3. Preferred acids include mineral acids, hydrogen sulfate, trifluoroacetic acid, formic acid, hydrobromic acid and acetic acid. A most preferred acid is hydrochloric acid. The resulting suspension is cooled and the product recovered by, for example, filtration. If desired, the isolated product can be washed with water, and dried, preferably at reduced pressure.

Some of the steps of the present invention may be carried out in one pot, as illustrated in the examples.

The valsartan synthesized may be obtained as various polymorphic forms in the sold state. Such forms are disclosed in U.S. Appl. No. 60/455,286, Filed on Mar. 17, 2003, entitled "Polymorphs of Valsartan and Processes for their Preparation", which is incorporated herein by reference.

Crude valsartan may be crystallized from organic solvents such as dichloromethane, diethyl ether or ethyl acetate. In a preferred embodiment, valsartan is crystallized from ethyl acetate. When crude material is crystallized out of ethyl acetate, the dry material may contain about 2.7% ethyl acetate by weight after conventional drying. The present invention provides for removing residual organic solvent such as ethyl acetate from the crude material. The crude valsartan, either wet or dry, preferably wet, containing residual solvent is triturated in water, in order to remove the residual solvent to acceptable levels (according to the ICH guidelines the level is limited to less than about 5000 ppm). In one embodiment, after trituration in water, the level of the residual solvent is 3600 ppm. Preferably the trituration is performed from about 4 to about 50° C., more preferably from about 25 to about 40° C. Preferably, the trituration is carried out for about 30 minutes to about 60 hours, more preferably from about 3 to about 20 hours.

Another manner to remove residual solvent, particularly ethyl acetate, is by performing a solvent exchange by contacting the solvate with humid gas in a fluidized bed apparatus. As used herein, the term "humid" refers to a relative humidity of at least 30%, more preferably at least about 50% and most preferably at least about 80%. A suitable fluidized bed apparatus is Retsch TG-100.

Pharmaceutical formulations/compositions of the present invention contain crystalline valsartan, such as one of those disclosed in U.S. Appl. No. 60/455,286, Filed on Mar. 17, 2003, entitled "Polymorphs of Valsartan and Processes for their Preparation", or valsartan purely amorphous, optionally in mixture with other form(s) of valsartan. The valsartan prepared by the processes of the present invention are ideal for pharmaceutical formulation since they are substantially free of the isoleucine analogue as an impurity. In addition to the active ingredient(s), the pharmaceutical compositions of the present invention may contain one or more excipients. Excipients are added to the composition for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, valsartan and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

The active ingredient and excipients may be formulated into compositions and dosage forms according to methods known in the art. The solid oral dosage forms disclosed in U.S. Pat. Nos. 6,485,745 and 6,395,728 may be used as a guidance. The dosages and formulation of DIOVAN may also be used for guidance. The dosage is preferably from about 10 mg to about 1280 mg, more preferably from about 20 mg to about 640 mg, and most preferably from about 40 mg to about 320 mg.

The present invention can be illustrated in one of its embodiments by the following non-limiting examples.

Preparation of Valsartan

EXAMPLE 1

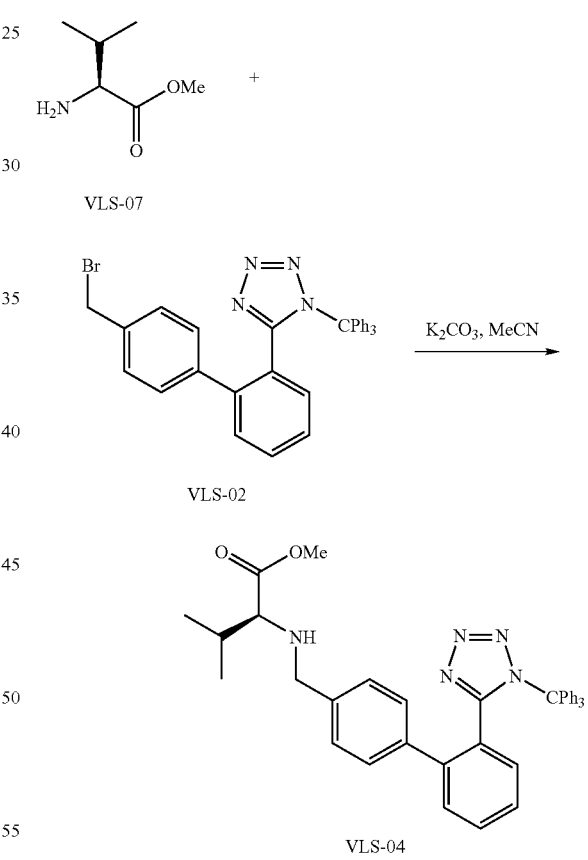

VLS-02 (30.0 g, 54.0 mmol) was added in one portion to the suspension of L-Valine methyl ester (free base, VLS-07, 10.6 g, 81.0 mmol, 1.5 eq) and $K_2CO_3$ (59.5 g, 4.3 mol, 8 eq) in dry Acetonitrile (200 mL) preheated to 50-60° C. The reaction was stirred for 2-3 h at 70° C. under Argon, cooled to 0° C. and filtered. The filtrate was evaporated under reduced pressure to give 36.0 g of crude VLS-04 as sticky yellow oil that was used in the next step without any purification.

EXAMPLE 2

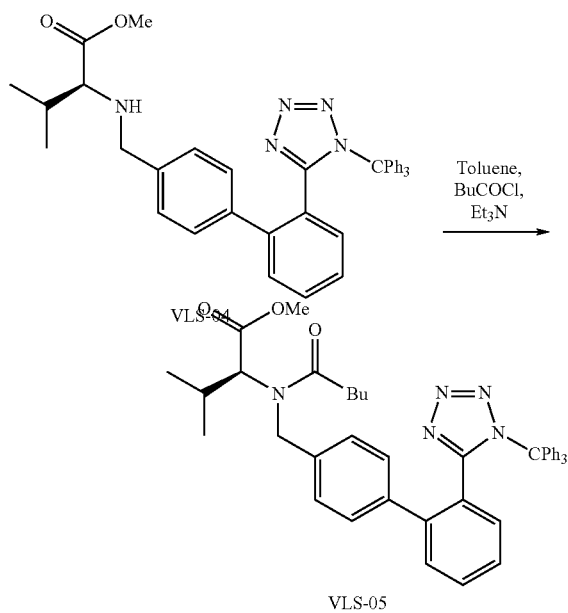

To solution of VLS-04 (36.0 g, 54 mmol) and Triethylamine (16.4 g, 22.5 mL, 162 mmol, 3.0 eq) in dry Toluene (200 mL) Valeroyl chloride (16.3 g, 16.0 mL, 0.135 mmol, 2.5 eq) was slowly added under Argon keeping the reaction temperature below 35° C. The resulted mixture was stirred for 10 h at room temperature and quenched with 10% aqueous solution of NaHCO$_3$ (100 mL). After stirring of 1 h at room temperature, the two-phase mixture was separated, the organic phase washed with 10% aqueous solution of NaHCO$_3$ (50 mL) and brine, dried over Na$_2$SO$_4$, filtered and evaporated under reduced pressure to give 44.0 g (near quant) of crude VLS-05 as yellow semisolid.

EXAMPLE 3

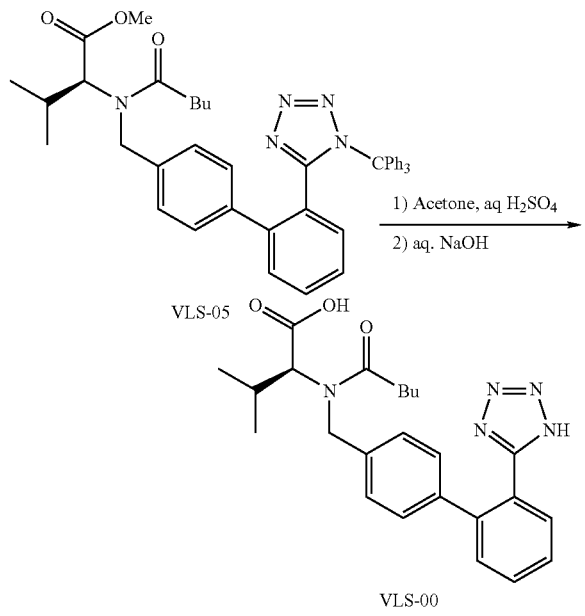

VLS-05 (15.0 g, 21.7 mmol) was dissolved in Acetone (90 mL), H$_2$SO$_4$ (98%, 3.5 mL, ~3 eq) in Water (20 mL) was slowly added and the resulted cloud solution was stirred for 5 h at room temperature (TLC or HPLC monitoring). A solution of NaOH (5.2 g, 130.2 mmol, 6 eq) in Water (10 mL) was slowly added, the resulted suspension was stirred for 12 h at room temperature and Acetone was evaporated under reduced pressure. The precipitate (TPM) was filtered and washed with Water (20 mL); the combined aqueous filtrate washed twice with total 50 mL of EtOAc and slowly acidified to pH 2.5 with 3N aqueous H$_2$SO$_4$. The resulted suspension was extracted twice with EtOAc (total 120 mL), the combined organics were washed with brine and concentrated to 50 mL volume under reduced pressure. This solution was cooled down to 0-4° C., stirred for 2 h and filtered to give 7.2 g of crude VLS-00 as a white solid. The crude was recrystallized from EtOAc afforded about 6.5 g of Valsartan as white powder.

EXAMPLE 4

Two samples of VLS-07 were tested for the level of isoleucine impurity by gas chromatography. One sample showed an impurity of 0.07%, another sample 0.30%. The sample with 0.07% was selected for preparation of valsartan according to examples 1-3.

EXAMPLE 5

Two samples of L-valine are tested for the level of isoleucine impurity by gas chromatography. One sample shows an impurity of 0.07%, another sample 0.30%. The sample with 0.07% is selected for preparation of valsartan according process of U.S. Pat. No. 5,399,578.

EXAMPLE 6

Two samples of VLS-07 are tested for the level of isoleucine impurity by gas chromatography. One sample shows an impurity of 0.07%, another sample 0.09%. Both samples are selected for preparation of valsartan according to examples 1-3.

Analytical Method for Valsartan:
Chromatography (HPLC)
Column: Luna 5 μm C18(2) 250 mm×4.6 mm (Phenomenex) Cat No. OOG-4252-EQ is suitable
Eluent: A: 0.1% Trifluoroacetic Acid in Acetonitrile B: 0.1% Trifluoroacetic Acid in Water
Gradient: 0 min—35% A/65% B, 15 min—35% A/65% B 40 min—80% A/20% B, 45 min—80% A/20% B
Flow rate: 1.0 mL/min
Detector: U at 215 nm
Column Temp.: 25° C.
Injection Vol.: 20 μL
Diluent: Eluent Component A/Component B 50/50 (v/v)
Note: All solvents and reagents should be HPLC or analytical grade.

Analytical Method for L-Valine Methyl Ester 3.0 GC Parameters
Column: DB-17 Capillary Column
Length—30 m, ID—0.53 mm
Stationary Phase—(50% Phenyl)Methylpolysiloxane Film—1 μm Temperature program:
 Hold at 45° C. for 5 min, increase to 220° C. at 10° C. per minute and hold at 220° C. for 4.5 min
Injector: 200° C.
Detector: FID
Detector temperature: 250° C.
Flow rate: Carrier gas—Helium, about 1.9 mL/min
Injection volume: 2.0 µL (split ratio 5:1)

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

What is claimed is:

1. A process for preparing valsartan that is substantially free of an impurity that is an isoleucine analogue of valsartan having the formula:

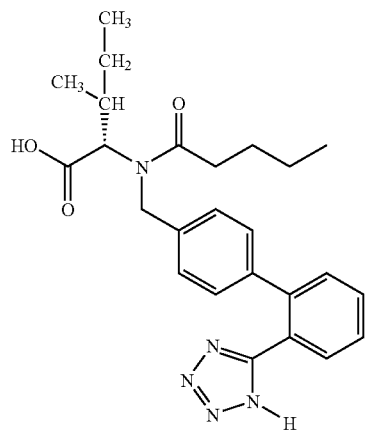

from an initial sample of L-valine or an L-valine ester, wherein the process comprises:
 a) analyzing the level of L-isoleucine or corresponding L-isoleucine ester present in at least one initial sample of L-valine or an L-valine ester at least at a single stage during the synthetic process to control the amount of said isoleucine analogue of valsartan;
 being present in the prepared valsartan
 b) selecting an initial sample of L-valine or an L-valine ester that has not more than about 0.1% as area percentage GC of the isoleucine analogue of said L-valine or L-valine ester; and
 c) reacting said initial sample of L-valine or L-valine ester with a biphenyl compound to synthesize said valsartan, that is substantially free of said isoleucine analogue of valsartan.

2. The process of claim 1 comprising the steps of:
 a) analyzing at least one sample of a $C_1$ to $C_4$ alkyl ester of L-valine for presence of the corresponding $C_1$ to $C_4$ alkyl ester of L-isoleucine as a impurity;
 b) selecting a sample of said $C_1$ to $C_4$ alkyl ester of L-valine that has not more than about 0.1% as area percentage GC of the-$C_1$ to $C_4$ alkyl ester of L-isoleucine;
 c) reacting compounds G2:

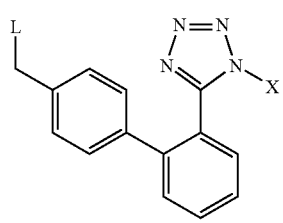

with the L-valine ester selected in step b) in a first organic solvent to obtain a compound G3:

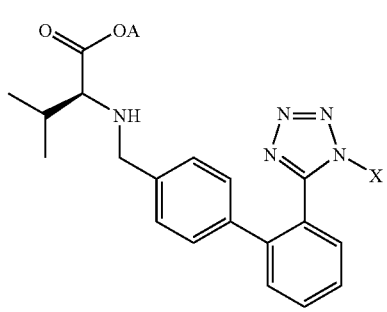

reacting compound G3 with an acylating agent in a second organic solvent to obtain a compound G4:

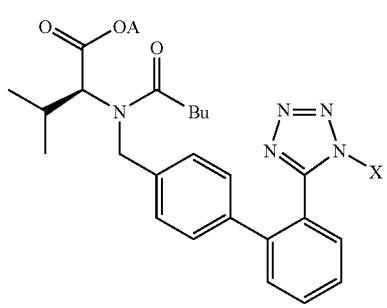

and
 e) hydrolyzing compound G4 to obtain valsartan;
 wherein A is a $C_1$ to $C_1$ alkyl group, X is a trityl group and L is leaving group.

3. The process of claim 1 wherein the level of the isoleucine analogue of valsartan is not more than 0.1% as area percentage HPLC.

4. The process of claim 3 wherein the valsartan contains less than about 0.07% of the corresponding isoleucine analogue of valsartan measured as an area percentage using HPLC.

5. The process of claim 3 wherein the level of L-isoleucine or the corresponding L-isoleucine ester in the batch of L-valine or L-valine ester of step (c) is less than about 0.07% measured as an area percentage GC.

6. The process of any one of claims 4, 5, 1 or 3, comprising analyzing the level of the corresponding L-isoleucine ester present in the initial sample of an L-valine ester.

7. The process of claim 6, wherein the initial sample of an L-valine ester is a methyl ester.

8. The process of claim 2, wherein the first and second organic solvents are independently selected from the group consisting of acetonitrile, toluene, acetone, ethyl acetate, dimethyl acetamide, DMF, hexane and mixtures thereof.

9. The process of claim 8, wherein step (c) is carried out in acetonitrile.

10. The process of claim 2, wherein the valsartan contains less than 0.1% of the isoleucine analogue of valsartan, measured as an area percentage HPLC.

11. The process of claim 1, wherein the L-valine ester that is analyzed is selected from methyl, ethyl, propyl, butyl, benzyl and aryl esters.

12. The process of claim 1, wherein the L-valine ester that is analyzed is a $C_1$ to $C_4$ alkyl ester.

13. The process of claim 12, wherein the L-valine ester that is analyzed is a methyl ester or a t-butyl ester.

* * * * *